(12) United States Patent
Zuo et al.

(10) Patent No.: US 9,087,369 B2
(45) Date of Patent: Jul. 21, 2015

(54) APPARATUS FOR BEING USED FOR DETECTING A PROPERTY OF AN OBJECT

(75) Inventors: Fei Zuo, Eindhoven (NL); Erik Godefridus Antonius Harks, Eindhoven (NL); Steven Antonie Willem Fokkenrood, 'S-Hertogenbosch (NL); Yingrong Xie, Eindhoven (NL); Szabolcs Deladi, Veldhoven (NL)

(73) Assignee: Koninklijke Philips N.V., Eindhoven (NL)

(*) Notice: Subject to any disclaimer, the term of this patent is extended or adjusted under 35 U.S.C. 154(b) by 120 days.

(21) Appl. No.: 13/884,624

(22) PCT Filed: Nov. 10, 2011

(86) PCT No.: PCT/IB2011/055017
§ 371 (c)(1),
(2), (4) Date: May 10, 2013

(87) PCT Pub. No.: WO2012/066455
PCT Pub. Date: May 24, 2012

(65) Prior Publication Data
US 2013/0230226 A1    Sep. 5, 2013

(30) Foreign Application Priority Data

Nov. 18, 2010  (EP) .................................... 10191687
Mar. 17, 2011  (EP) .................................... 11158581

(51) Int. Cl.
*G06K 9/00* (2006.01)
*G06T 7/00* (2006.01)
(Continued)

(52) U.S. Cl.
CPC ............... *G06T 7/0012* (2013.01); *A61B 8/085* (2013.01); *A61B 8/0858* (2013.01); *A61B 8/12* (2013.01);
(Continued)

(58) Field of Classification Search
CPC ............... A61B 8/00; A61N 5/00; A61N 7/00
USPC ......... 382/128, 129, 130, 131, 132, 133, 134; 600/407, 410, 425, 427, 439, 468; 607/119; 378/4, 8, 21–27, 901
See application file for complete search history.

(56) References Cited

U.S. PATENT DOCUMENTS 5,222,501 A * 6/1993 Ideker et al. ................... 600/439
6,358,208 B1 * 3/2002 Lang et al. ..................... 600/438

FOREIGN PATENT DOCUMENTS

EP        0876796      11/1996
WO        WO0051513    9/2000
(Continued)

OTHER PUBLICATIONS

H.K. Chiang et al., "In-Virto Ultrasound Temperature Monitoring in Bovine Liver During RF Ablation Therapy Using Autocorrelation", IEEE Ultrasonics Symp. 2002, pp. 1439-1442.
(Continued)

*Primary Examiner* — Abolfazl Tabatabai

(57) ABSTRACT

The invention relates to an apparatus for being used for detecting a property of an object. An ultrasound signal providing unit (2) provides an ultrasound signal, which is indicative of a property of the object (9) at one or several depths within the object (9) and which depends on time, and a periodicity value determination unit (5) determines a periodicity value being indicative of a degree of temporal periodicity of the ultrasound signal for a constant depth. The temporal periodicity of the ultrasound signal at the respective constant depth, i.e. the periodicity value, depends on the property of the object at this depth and can therefore be used for detecting a property of the object.

15 Claims, 7 Drawing Sheets

(51) Int. Cl.
  *A61B 8/08* (2006.01)
  *A61B 8/12* (2006.01)
  *A61B 18/14* (2006.01)
  *A61B 5/05* (2006.01)
  *A61B 18/02* (2006.01)
  *A61B 18/18* (2006.01)
  *A61B 17/00* (2006.01)
  *A61N 7/00* (2006.01)

(52) U.S. Cl.
  CPC ............ *A61B 8/5223* (2013.01); *A61B 18/1492* (2013.01); *A61B 18/02* (2013.01); *A61B 18/18* (2013.01); *A61B 2017/00106* (2013.01); *A61N 7/00* (2013.01)

(56) References Cited

FOREIGN PATENT DOCUMENTS

| WO | WO0170114 | 9/2001 |
| WO | WO2006044996 | 4/2006 |
| WO | WO2010082146 | 7/2010 |

OTHER PUBLICATIONS

D. Mast et al., "Ultrasound Monitoring of In Vitro Radio Frequency Ablation by Echo Decorrelation Imaging", J. Ultrasound Med., 2008, 27, pp. 1685-1697.

* cited by examiner

APPARATUS FOR BEING USED FOR DETECTING A PROPERTY OF AN OBJECT

FIELD OF THE INVENTION

The invention relates to an apparatus, a method and a computer program for being used for detecting a property of an object.

BACKGROUND OF THE INVENTION

The article "In-Vitro Ultrasound Temperature Monitoring in Bovine Liver during RF Ablation Therapy using Autocorrelation", Huihua Kenny Chiang et al., pages 1539 to 1552, IEEE Ultrasonic Symposium, 2002 discloses an apparatus for determining a two-dimensional temperature distribution in bovine liver tissue based on radio frequency (RF) ultrasound signals. The two-dimensional temperature map is used for thermal dosage control and real-time temperature monitoring during RF thermal therapy.

This apparatus has the drawback that an ablation therapy is not directly monitored, i.e. the apparatus does not provide direct information about the ablation status of the bovine liver tissue. Only the two-dimensional temperature map is determined, which only gives an indirect and inaccurate impression about the ablation status. A control of the ablation based on the two-dimensional temperature map is therefore also inaccurate.

SUMMARY OF THE INVENTION

It is an object of the present invention to provide an apparatus, a method and a computer program for being used for detecting a property of an object, wherein the detection of a property of the object can be improved.

In a first aspect of the present invention an apparatus for being used for detecting a property of an object is presented, wherein the apparatus comprises:

an ultrasound signal providing unit for providing an ultrasound signal, which is indicative of a property of the object at one or several depths within the object and which depends on time, a periodicity value determination unit for determining a periodicity value being indicative of a degree of temporal periodicity of the ultrasound signal for a constant depth.

The temporal periodicity of the ultrasound signal at the respective constant depth depends on the property of the object at this depth. Thus, by determining a periodicity value being indicative of a degree of temporal periodicity of the ultrasound signal for a constant depth, a value is provided which is indicative of a property of the object at the respective depth. This periodicity value can be used for detecting a property of the object directly with improved quality.

The property, which can be detected by using the apparatus, can be whether a sensed region of the object undergoes a structural change at the respective depth or not. In particular, the object is preferentially a heart of a person or of an animal and the property is, for example, whether a certain region of the heart tissue comprises healthy tissue, coagulated tissue or is a transition region between healthy tissue and coagulated tissue. In the transition region, the tissue structure is changed by breaking up healthy tissue structures, i.e. in the transition region the tissue structure undergoes a structural change, whereas in the regions comprising healthy tissue and coagulated tissue the tissue structure does not change. The transition region corresponds to a lesion boundary, which may be detected by using the determined periodicity value. Thus, the apparatus can further comprise a lesion boundary determination unit for determining a lesion boundary, which is generated by applying energy to the object, depending on the determined periodicity value. The lesion boundary determination unit is preferentially adapted to determine a lesion boundary generated by applying ablation energy to the object for ablating the same. In particular, the apparatus is preferentially adapted to determine a boundary of a lesion within a heart, which is generated by ablating the heart. In an embodiment, the lesion boundary determination unit determines the lesion boundary in realtime, thereby allowing a realtime monitoring of the ablation procedure.

It is preferred that the lesion boundary determination unit is adapted to determine the lesion boundary by thresholding the periodicity value. For example, if at a certain time and at a certain depth the periodicity value is smaller than a predefined threshold, the lesion boundary determination unit can determine that a lesion boundary is present at the certain time and at the certain depth. The threshold can be predetermined by, for example, calibration measurements, wherein periodicity values are determined for an object having a lesion boundary at a known location and wherein the threshold is predetermined such that a location of a lesion boundary determined by using the threshold matches as good as possible the known location of the real lesion boundary.

The temporal periodicity preferentially defines how regularly a condition or an event occurs at the respective depth with increasing time. For example, it defines how regularly substantially the same ultrasound reflectivity occurs at the respective depth with increasing time. The temporal periodicity value could therefore also be regarded as being a regularity value being indicative of how regularly a condition or an event occurs at the respective depth with increasing time.

It is also preferred that the apparatus comprises an energy application unit for applying energy to the object and a control unit for controlling the energy application unit depending on the determined lesion boundary. The energy application unit is preferentially an ablation unit for ablating the object. The energy application unit can comprise ablation electrodes for applying electrical energy, in particular, RF energy, or optical elements for applying light energy, for example, optical fibers. The energy application unit can also comprise a cryo-ablation element, a high intensity focused ultrasound element and/or a microwave element for ablating the object.

The control unit can be adapted to control the energy application unit, in particular, the ablation unit, by controlling the power and/or duration of applying ablation energy to the object depending on the determined lesion boundary. If a heart wall is ablated and the thickness of the wall is known, the control unit can be adapted to control the energy application unit depending on the thickness and the determined ablation depth, i.e. the depth of the lesion boundary. Preferentially, the control unit is adapted to ablate a heart wall until a desired ablation depth has been reached, in particular, until the resulting lesion is transmural.

The lesion boundary determination unit can be adapted to determine the position of a front surface and a back surface of the heart wall from the ultrasound signal. In particular, the lesion boundary determination unit can be adapted to determine the thickness of the wall from the determined positions of the front surface and the back surface of the wall. Thus, the ultrasound signal can be used for determining the ablation depth and for determining the thickness of the wall, i.e. in an embodiment it is not necessary to provide a further unit for measuring the wall thickness. The thickness of the wall, the ablation depth and the degree of transmurality can be determined by using the ultrasound signal only.

The ultrasound signal providing unit can be adapted to provide an ultrasound signal produced by sending ultrasound pulses out to the object, receiving dynamic echo series after the ultrasound pulses have been reflected by the object, and generating the ultrasound signal depending on the received dynamic echo series.

If an ultrasound pulse is sent out to the object, the ultrasound pulse is reflected at different depths such that echo signals are received by the ultrasound signal providing unit at different times. The echo signals, which are generated by reflection of the ultrasound pulse at different depths within the object, form an echo series. By considering the speed of sound and the time, when an echo is recorded after the ultrasound pulse has been sent out into the object, the echo series can be translated into a dependence of an ultrasound reflection property of the object on the depth within the object.

Furthermore, preferentially several ultrasound pulses are sent out to the object at different times, thereby generating echo series at different times. These echo series, which are obtained from different ultrasound pulses at different times and, thus, which belong to different times, form dynamic echo series. The ultrasound signal which depends on the received dynamic echo series represents therefore the ultrasound reflection properties of the object at different depths and at different times.

The ultrasound signal providing unit can be any unit that provides the ultrasound signal. For example, the ultrasound signal providing unit can be a storing unit in which produced ultrasound signals are stored or it can be an ultrasound signal receiving unit for receiving a generated ultrasound signal, which can be provided to further units for processing the ultrasound signal. The ultrasound signal providing unit can also be an ultrasound measurement unit for measuring the ultrasound signal.

The ultrasound signal that depends on the received dynamic echo series can be represented as a two-dimensional image showing a reflection intensity depending on two-dimensions, for example, depending on the time on a horizontal axis and depending on the depth on a vertical axis. This two-dimensional image can also be regarded as an M-mode image. The periodicity value determination unit can be adapted to determine periodicity values for this two-dimensional image, wherein a lesion boundary can be determined by, for example, indentifying regions in the two-dimensional image, in which the periodicity values are below a predefined threshold. The ultrasound signal that depends on the received dynamic echo series can also be represented as a three- or four-dimensional image showing a reflection intensity depending on the time and two or three spatial dimensions, respectively. This allows determining the lesion boundary in different directions in which ultrasound pulses have been sent out into the object.

The lesion boundary determination unit can be adapted to determine the lesion boundary at different times from the M-mode image, thereby determining the progression of the lesion boundary.

It is preferred that the object is a periodically moving object, wherein the apparatus comprises a filtering unit for temporally filtering the ultrasound signal, before determining the periodicity value, for a constant depth with a band-pass which includes a frequency of the periodic movement of the object. The object is preferentially a heart of a person or of an animal and the filtering unit can be adapted to allow temporal frequencies of the ultrasound signal to pass the filtering unit, which are within a predefined frequency range of possible heart frequencies. It is further preferred that the apparatus comprises a frequency determination unit for determining the frequency of the periodic movement of the object, wherein the filtering unit is adapted to temporally filter the ultrasound signal for a constant depth with a band-pass which includes the determined frequency of the periodic movement. This allows to adapt the filtering to the currently determined frequency of the periodic movement, thereby improving the filtering of the ultrasound signal, if the frequency of the periodic movement of the object is not constant.

Thus, the filtering unit can provide an adaptive band-pass which is adapted to the respective actually determined frequency of the periodic movement of the object. For example, the band-pass can have a predefined absolute or relative frequency range, which can be centered on the actually determined frequency of the periodic movement.

In particular, the temporal periodicity of the ultrasound signal for a constant depth can be caused by a periodic movement of the object. The degree of the periodicity in a respective region within the object, which is sensed by the ultrasound signal, can depend on the structure of the object within the respective region, wherein the structure defines how the respective region follows the overall periodic movement of the object. The periodicity value can therefore be indicative of a periodicity having a frequency defined by the periodic movement of the object. By temporally filtering the ultrasound signal with a band-pass which includes a frequency of the periodic movement of the object, parts of the ultrasound signal, which should not contribute to the periodicity value, can be filtered out, thereby improving the quality of determining a periodicity value based on the filtered ultrasound signal.

The frequency determination unit can comprise a unit for measuring electrocardiography (ECG) signals. For example, if an ablation electrode is used for ablating heart tissue, the ablation electrode or another electrode can be adapted to measure local electrical activation at the ablation site. This local electrical activation can be periodic, in particular, substantially sinusoidal, and can be used to determine the periodicity, i.e. the heart rate, of the movement of the heart, which can define the actual band-pass of the filtering procedure. If the local electrical activation indicates atrial fibrillation (AF), the inverse temporal cardiac cycle length could be used as the frequency on which a predefined absolute or relative frequency range of the band-pass can be centered.

The frequency determination unit can also be adapted to determine the frequency of the periodic movement from the ultrasound signal. For example, if the object is a heart and the apparatus is adapted to detect a property within the heart tissue, in particular, if the apparatus is adapted to detect a lesion boundary within the heart tissue, the frequency determination unit can be adapted to determine a periodic change of the part of the ultrasound signal, which corresponds to a front surface or a back surface of a heart wall, and to determine the frequency of this periodic change as the frequency of the periodic movement of the heart.

The periodicity value determination unit can be adapted to determine the periodicity value depending on a temporal auto-correlation of the ultrasound signal for a constant depth. In particular, the periodicity value determination unit can be adapted to determine the periodicity value depending on a normalized temporal auto-correlation value of the ultrasound signal for a constant depth.

Preferentially, the periodicity value determination unit is adapted to determine the periodicity value depending on one or several peak values at non-zero shift locations of the temporal auto-correlation of the ultrasound signal for a constant depth. The periodicity value determination unit can particularly be adapted to determine a peak value at a non-zero shift location or a combination of peak values at non-zero shift locations, for example, an average of several peak values at non-zero shift locations, of the temporal auto-correlation of the ultrasound signal as the periodicity value. For example, the periodicity value determination unit can be adapted to determine the periodicity value depending on a first peak value of a first peak at a non-zero shift location, which is neighbored to a peak at a zero shift location of the temporal auto-correlation of the ultrasound signal for a constant depth. The first peak at a non-zero shift location corresponds preferentially to a shift by one period of a periodic movement of the object, in particular, to one cardiac cycle if the object is a heart. By using the auto-correlation one or several periodic values can be determined in a relative simple way.

It is preferred that the periodicity value determination unit is adapted to determine different ultrasound signal segments, which correspond each to a constant depth and to a temporal segmentation duration, and to determine for the different ultrasound signal segments periodicity values. The lesion boundary determination unit is then preferentially adapted to determine a lesion boundary depending on the several periodicity values. Also in this case the lesion boundary determination unit can be adapted to determine the lesion boundary by thresholding the respective periodicity value. For example, if for a certain ultrasound signal segment a periodicity value has been determined, which is smaller than a predefined threshold value, it can be determined that the certain ultrasound signal segment is located at a lesion boundary.

The temporal segmentation duration is preferentially predefined. The temporal segmentation duration can be predefined by calibration measurements, wherein the position of the lesion boundary is known and the temporal segmentation duration is defined such that the determined position of the lesion boundary matches as good as possible the known real position of the lesion boundary.

It is also preferred that the apparatus comprises a display for showing the periodicity values depending on the depths and temporal positions of the respective ultrasound signal segments for which the periodicity values have been determined. The display can be adapted to further show a determined lesion boundary and/or the ultrasound signal. For example, the determined lesion boundary can be shown as a line on the periodicity values or on an M-mode image, if the ultrasound signal is an M-mode image.

A user like a physician can look on the display showing at least the periodicity values, which are indicative of the lesion boundary, and can, for example, control an ablation procedure based on the displayed periodicity values.

It is further preferred that the apparatus comprises a catheter, wherein the ultrasound signal providing unit is located within the catheter. This allows operating the apparatus within a hollow object like a heart. Furthermore, since the ultrasound can be arranged close to an inner surface of the object, high-frequency ultrasound can be used, if the object is living tissue, although high-frequency ultrasound has a small penetration depth only. Preferentially also the energy application unit is located within or at the catheter.

In a further aspect of the invention a method for being used for detecting a property of an object is presented, wherein the method comprises:

providing an ultrasound signal, which is indicative of a property of the object at one or several depths within the object and which depends on time, by an ultrasound signal providing unit, determining a periodicity value being indicative of a degree of temporal periodicity of the ultrasound signal for a constant depth by a periodicity value determination unit.

In a further aspect of the invention a computer program for being used for detecting a property of an object is presented, wherein the computer program comprises program code means for causing an apparatus as defined in claim 1 to carry out the steps of the method as defined in claim 14, when the computer program is run on a computer controlling the apparatus.

It shall be understood that the apparatus of claim 1, the method of claim 14, and the computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
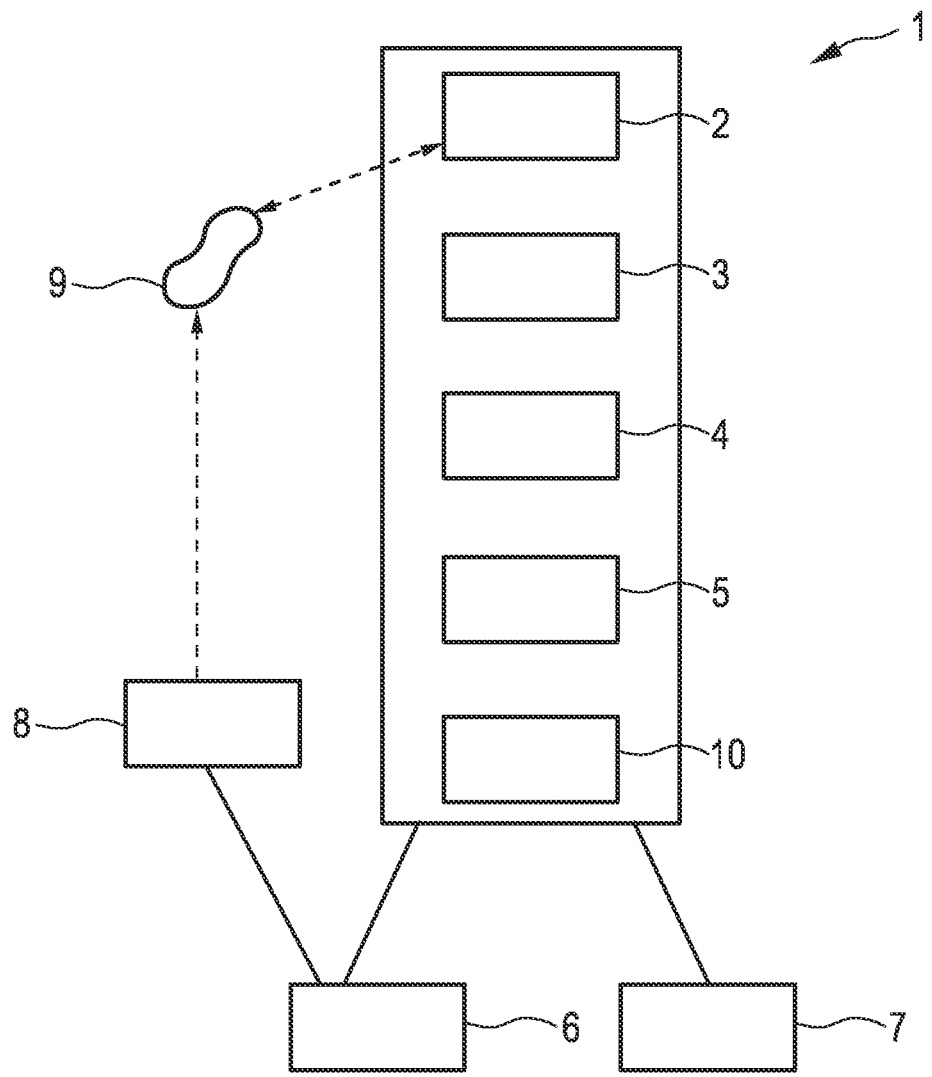
FIG. 1 shows schematically and exemplarily an embodiment of an apparatus for being used for detecting a property of an object.

FIG. 1 shows schematically and exemplarily an embodiment of an apparatus for being used for detecting a property of an object. The apparatus 1 comprises an ultrasound signal providing unit 2 for providing an ultrasound signal being indicative of a property of the object 9 at one or several depths within the object 9 and depending on time. The object is, in this embodiment, a heart of a person, in particular, a heart wall.

The ultrasound signal providing unit 2 is adapted to send ultrasound pulses out to the object 9, to receive dynamic echo series after the ultrasound pulses have been reflected by the object 9, and to generate the ultrasound signal depending on the received dynamic echo series.

If an ultrasound pulse is sent out to the object, the ultrasound pulse is reflected at different depths such that echo signals are received by the ultrasound signal providing unit 2 at different times. The echo signals, which are generated by reflection of the ultrasound pulse at different depths within the object, form an echo series. By considering the speed of sound and the time, when an echo is recorded after the ultrasound pulse has been sent out into the object, the echo series can be translated into a dependence of an ultrasound reflection property of the object on the depth within the object. Furthermore, several ultrasound pulses are sent out to the object 9 at different times, thereby generating echo series at different times. These echo series, which are obtained from different ultrasound pulses at different times and, thus, which belong to different times, form dynamic echo series. The ultrasound signal which depends on the received dynamic echo series represents therefore the ultrasound reflection properties of the object at different depths and at different times.

The ultrasound signal that depends on the received dynamic echo series can be represented as a two-dimensional image showing a reflection intensity depending on two-dimensions, for example, depending on the time on a horizontal axis and depending on the depth on a vertical axis. A corresponding two-dimensional M-mode image is exemplarily shown in FIG. 2.

Figure 2:
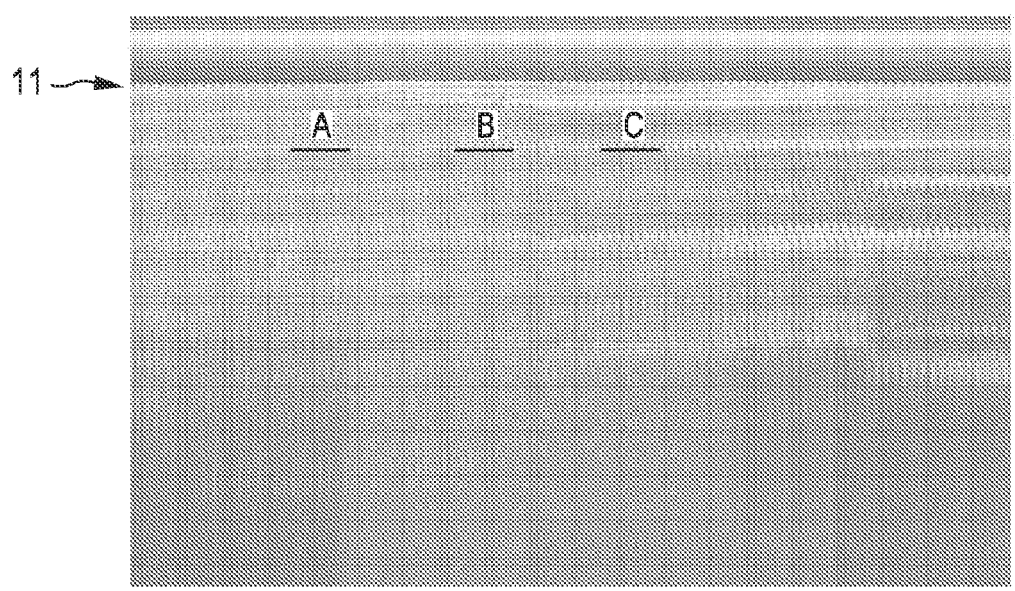
FIG. 2 shows exemplarily several ultrasound signal segments in an M-mode image.

The apparatus 1 further comprises a frequency determination unit 3 for determining the frequency of the periodic movement of the heart 9. In this embodiment, the frequency determination unit 3 is adapted to determine the frequency of the periodic movement from the ultrasound signal, in particular, from the M-mode image. In FIG. 2, the arrow 11 indicates a depth within the heart tissue, which corresponds to a front surface or a back surface of a heart wall. The frequency determination unit 3 is adapted to determine the frequency of the periodic change in the M-mode image at the depth indicated by the arrow 11 as the frequency of the periodic movement of the heart 9. In another embodiment, the frequency determination unit can be adapted to determine the periodicity of the movement of the object in another way. For example, the frequency determination unit can comprise a unit for measuring ECG signals. For instance, if an ablation electrode is used for ablating heart tissue, the ablation electrode or another electrode can be adapted to measure local electrical activation at the ablation site. This local electrical activation can be periodic, in particular, substantially sinusoidal, and can be used to determine the periodicity, i.e. the heart rate, of the movement of the heart. Also the inverse temporal cardiac cycle length could be used as the frequency of the periodic movement of the heart 9, in particular, if AF is present.

The apparatus 1 further comprises a filtering unit 4 for temporarily filtering the ultrasound signal for a constant depth with a band-pass which includes the determined frequency of the periodic movement of the object 9. The filtering unit 4 is therefore adapted to provide an adaptive band-pass which is adapted to the respective actually determined frequency of the periodic movement of the object 9. For example, the band-pass can have a predefined absolute or relative frequency range, which can be centered on the actually determined frequency of the periodic movement.

The apparatus 1 further comprises a periodicity value determination unit 5 for determining a periodicity value being indicative of a degree of temporal periodicity of the ultrasound signal for a constant depth. In this embodiment, the periodicity value determination unit 5 is adapted to determine the periodicity value depending on a normalized temporal auto-correlation value of the ultrasound signal for a constant depth. In particular, the periodicity value determination unit 5 can be adapted to determine the periodicity value depending on one or several peak values at non-zero shift locations of the temporal auto-correlation of the ultrasound signal for a constant depth. For example, a first peak value of a first peak at a non-zero shift location, which is neighbored to a peak at a zero shift location of the temporal auto-correlation of the ultrasound signal for a constant depth, can be determined as the periodicity value. Moreover, a combination of the peak values of peaks at non-zero shift locations of the temporal auto-correlation of the ultrasound signal can be determined as the periodicity value. For example, an average of these non-zero shift peak values can be determined as the periodicity value.

In this embodiment, the periodicity value determination unit 5 is adapted to determine different ultrasound signal segments, which correspond each to a constant depth and to a temporal segmentation duration, and to determine for the different ultrasound signal segments periodicity values. The temporal segmentation duration is preferentially predefined such that it covers at least two cardiac cycles. In particular, the temporal segmentation duration can be predefined such that it covers three to six cardiac cycles. For example, the temporal segmentation duration can be at least four seconds and is preferentially within the range of six to twelve seconds, wherein a largest expected cardiac cycle of two seconds is assumed. In an embodiment, the temporal segmentation duration is not predefined, but adapted to the currently measured frequency of the periodic movement of the object. The temporal segmentation duration can be determined as a predefined multiple of the actually measured frequency of the movement of the object. For instance, the temporal segmentation duration can be at least twice of the inverse of the actually measured frequency, preferentially three times to six times the inverse of the actually measured frequency.

FIG. 2 shows exemplarily an M-mode image and three ultrasound signal segments A, B and C. Each ultrasound signal segment has a temporal segmentation duration W starting at the time t. Thus, each ultrasound signal segment belongs to a time window that can be defined by [t, t+W]. The respective ultrasound signal segment, i.e. a horizontal segment in the M-mode image shown in FIG. 2, at a constant depth d can then be denoted by f(d, t), wherein f is a vector of length W.

The ultrasound signal and, thus, the ultrasound signal segments, are preferentially filtered by the filtering unit 4 as described above. In particular, the ultrasound signal is band-pass filtered such that only frequencies having a frequency range, which includes the frequency of the periodic movement of the heart, pass the filtering unit 4. The frequency range can have a relatively narrow bandwidth of, for example, 0.5 Hz to 3 Hz, which covers the range of heart rates from 30 beats/min to 180 beats/min.

The normalized auto-correlation function C(f(d,t),l) can, for example, be calculated in accordance with following equation:

$$C(f(d,t),l) = \sum_{t'} u(d,t')u(d,t'-l)$$

with $$t' = t \ldots t+W,$$

wherein u(d,t') denotes the ultrasound signal at the depth d and the time t' and l denotes the lag. The lag l is preferentially larger than −maxlags and smaller than +maxlags, i.e. maxlags defines the maximum lags used for calculating C. Preferentially, the variable maxlags has a value which corresponds to a temporal duration being larger than a maximally possible cardiac cycle. For example, maxlags can have a value of half the length of the respective ultrasound signal segment.

Figure 3:
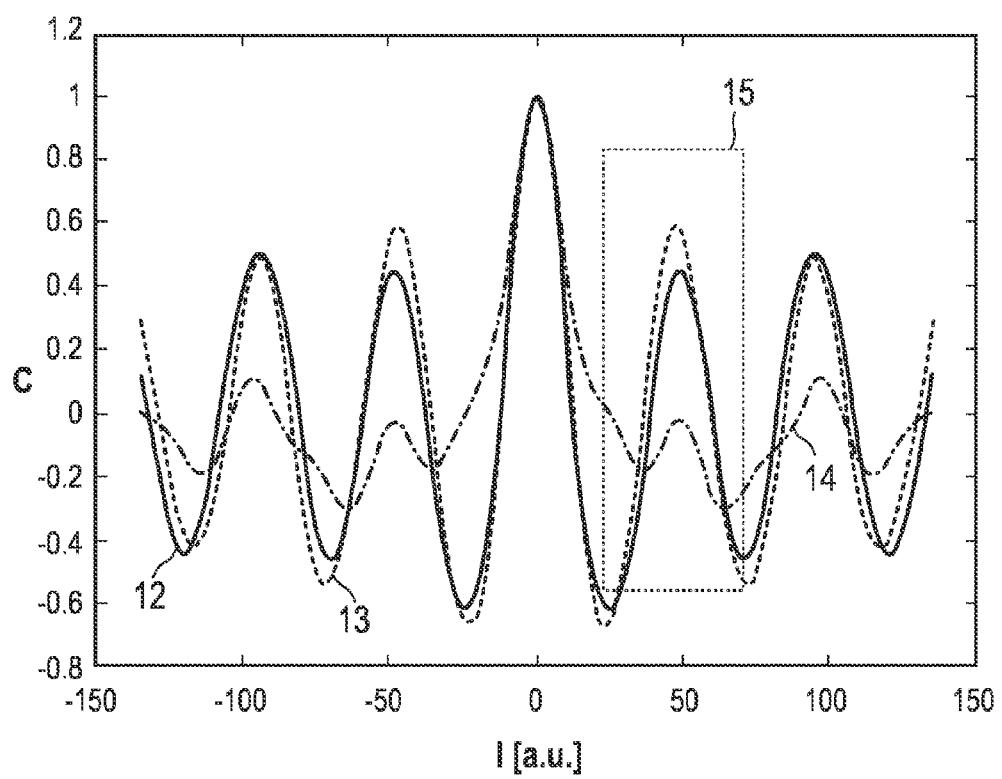
FIG. 3 shows exemplarily several auto-correlation functions.

FIG. 3 shows schematically and exemplarily three auto-correlation functions 12, 13, 14, which correspond to the three ultrasound signal segments A, B, C shown in FIG. 2. In FIG. 3, the normalized correlation value C is shown depending on the lag l, i.e. the shift in time-line, in arbitrary units. The first ultrasound signal element A corresponds to a region before ablation, the second ultrasound signal segment B corresponds to a region during ablation and the ultrasound signal segment C corresponds to a region in which the lesion stabilizes. The lesion front or lesion boundary is therefore in the region covered by the second ultrasound signal segment B. The dashed box 15 shown in FIG. 3 includes a first peak at a non-zero shift location, which is neighbored to a peak at a zero shift location of the respective temporal auto-correlation function. This first peak corresponds to a shift, i.e. a lag, by one cardiac cycle. In an embodiment, the periodicity value determination unit 5 is adapted to determine the peak value of the peaks within the dashed box 15 as the periodicity value, which can be denoted as P(f(t,d)). As can be seen in FIG. 3, the auto-correlation functions 12, 13, which correspond to the first and third ultrasound signal segments A, C, have a periodicity value, i.e. a peak value of a first non-zero shift peak, being larger than the corresponding periodicity value of the auto-correlation function 14, which corresponds to the second ultrasound signal segment B.

The apparatus 1 further comprises a lesion boundary determination unit 10 for determining a lesion boundary, which is generated by applying energy to the heart 9, depending on the determined periodicity value. The lesion boundary determination unit 10 is preferentially adapted to determine a lesion boundary generated by applying ablation energy to the heart 9 for ablating the same. In particular, the lesion boundary determination unit 10 is adapted to determine the lesion boundary by thresholding the periodicity value. For example, if at a certain time t and at a certain depth d the periodicity value P(f(t,d)) is smaller than a predefined threshold, the lesion boundary determination unit 10 can determine that a lesion boundary is present at the certain time t and at the certain depth d. The threshold can be predetermined by, for example, calibration measurements, wherein periodicity values are determined for cardiac tissue having a lesion boundary at a known location and wherein the threshold is predetermined such that a location of a lesion boundary determined by using the threshold matches as good as possible the known location of the lesion boundary. For example, with reference to FIG. 3, the threshold can be predefined such that the peak value of the auto-correlation function 14 within the dashed box 15 is below the threshold and the peak values of the auto-correlation functions 12 and 13 within the dashed box 15 are above the threshold.

The lesion boundary determination unit is therefore preferentially adapted to determine whether a lesion boundary is present at different times t and at different depths d based on the periodicity values P(f(t,d)). The lesion boundary determination unit 10 can, for example, be adapted to determine the progression of the lesion boundary within the cardiac tissue.

The apparatus 1 further comprises an energy application unit 8 for applying energy to the heart 9 and a control unit 6 for controlling the energy application unit 8 depending on the determined lesion boundary. The energy application unit 8 is preferentially adapted to apply electrical energy, in particular, RF energy, by using ablation electrodes. The energy application unit 8 can also be adapted to apply light energy for ablating cardiac tissue by using, for instance, optical fibers. Moreover, the energy application unit 8 can also comprise a cryo-ablation element, a high intensity focused ultrasound element and/or a microwave element for ablating cardiac tissue.

The control unit 6 is adapted to control the energy application unit 8 by controlling the power and/or duration of applying energy, in this embodiment, ablation energy, to the heart 9 depending on the determined lesion boundary. Preferentially, the heart wall is ablated and the thickness of the wall is known, wherein the control unit 6 controls the energy application unit 8 depending on the thickness and the determined ablation depth, i.e. the depth of the determined lesion boundary. The control unit 6 is preferentially adapted to ablate a heart wall until a desired ablation depth has been reached, in particular, until the resulting lesion is transmural.

The thickness of the wall is preferentially also determined by the lesion boundary determination unit 10. In particular, the lesion boundary determination unit 10 is adapted to determine the position of a front surface and a back surface of the heart wall from the ultrasound signal and to determine the thickness of the wall from these determined positions of the front surface and the back surface of the wall. Thus, the ultrasound signal can be used for determining the lesion boundary and for determining the thickness of the wall, i.e. it is, in this embodiment, not necessary to provide a further unit for measuring the wall thickness. The thickness of the wall, the lesion boundary, i.e. the ablation depth, and the degree of transmurality can be determined by using the ultrasound signal only.

The determination of the front surface and the back surface of the heart wall will in the following be described in more detail with reference to FIG. 4.

Figure 4:
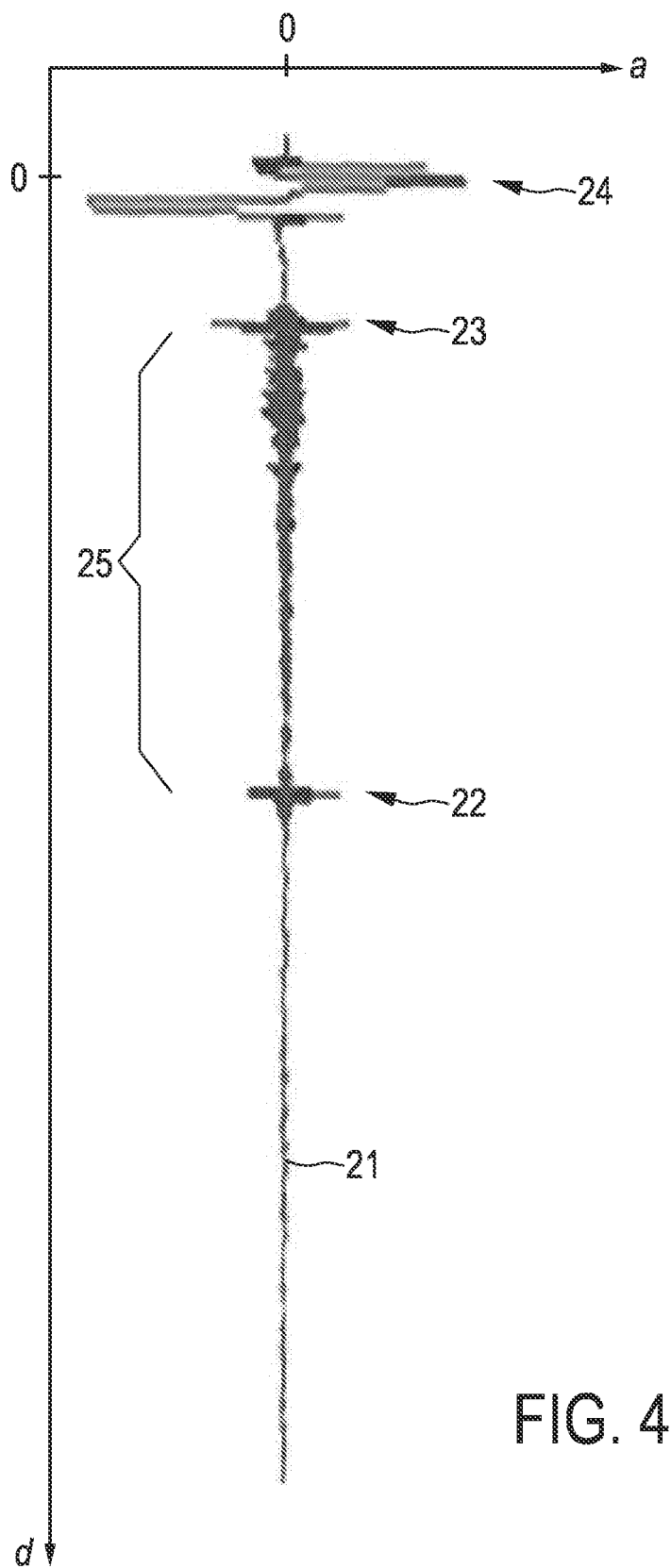
FIG. 4 shows exemplarily an echo series of an ultrasound signal, which corresponds to an A-line.

FIG. 4 shows exemplarily an A-line of the ultrasound signal, which corresponds to the ultrasound amplitudes along a vertical line in an M-mode image at a certain time t.

If an ultrasound pulse is sent out to the object 9, the ultrasound pulse is reflected at different depths and echo signals are received. The echo signals, which are generated by reflection of the ultrasound pulse at different depths within the object 9, form an echo series 21, i.e. an A-line, as exemplarily shown in FIG. 4. By considering the speed of sound and the time, at which an echo is recorded after the ultrasound pulse has been sent out to the object 9, the echo series can be translated into a dependence of an ultrasound reflection property of the object 9 on the depth within the object. In FIG. 4, the amplitude a of the echo series in arbitrary units, which corresponds to the ultrasound reflection property, is shown depending on the depth d in arbitrary units.

In FIG. 4, the regions of the echo series 21 denoted by 22 and 23, correspond to front and back surfaces of the heart wall. The region 24 is directly generated by the ultrasound pulse. Thus, in a strict sense, the echo series is the graph shown in FIG. 4 without region 24.

The echo series 21 shown in FIG. 4 allows determining the position of the front and back surfaces 22, 23 with respect to the position of an ultrasound unit that emits the ultrasound pulse and receives the echoes. The first measured amplitude in the region 24 marks the position of an ultrasound transducer. Region 24 is followed by a region comprising an amplitude being substantially zero and after a while the amplitude increases again in region 23 marking the first reflection at the object, i.e. marking the front surface of the object 9. A region 25 comprising smaller amplitudes that correspond to reflections within the tissue of the heart wall follows, and then in the region 22 the amplitude increases again significantly thereby marking the back surface of the heart wall. Thus, the echo series 21 allows determining the positions of the front and back surfaces based on the regions 22 and 23.

Figure 5:
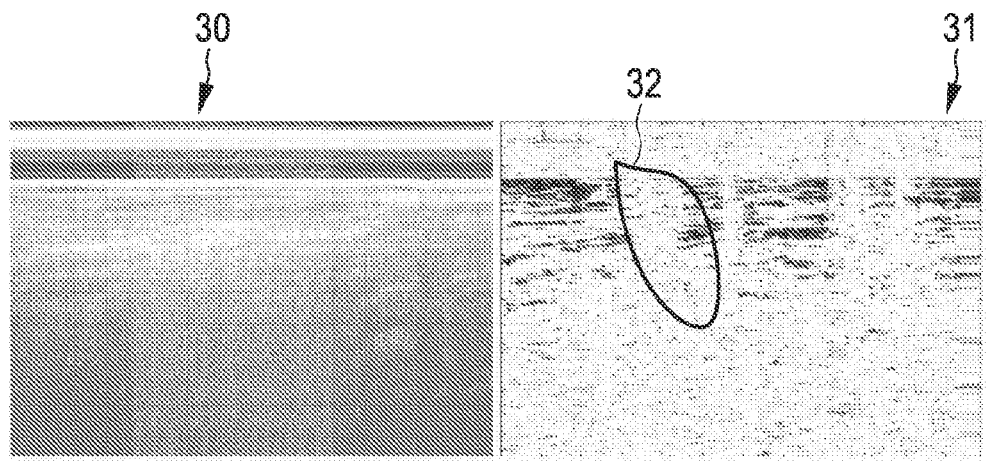
FIG. 5 shows exemplarily an M-mode image and a corresponding two-dimensional representation of periodicity values.

The apparatus 1 further comprises a display 7 for showing the periodicity values P(f(t,d)) depending on the depth d and temporal positions t of the respective ultrasound signal segments for which the periodicity values have been determined. The display 7 can further be adapted to show a determined lesion boundary and/or the ultrasound signal, in particular, the M-mode image. FIG. 5 shows schematically and exemplarily an M-mode image 30 and a two-dimensional visualization of the periodicity values P(f(t,d)), which can be provided on the display 7. A closed line 32 indicates a region having periodicity values which correspond to a lesion boundary. The closed line 32 may not be shown on the display 7. The representation 31 of the periodicity values can be used by a physician to monitor the progression of a lesion boundary during an ablation procedure, even if, in an embodiment, a lesion boundary is not automatically determined. In the representation 31 different periodicity values are assigned to different colors.

Figure 6:
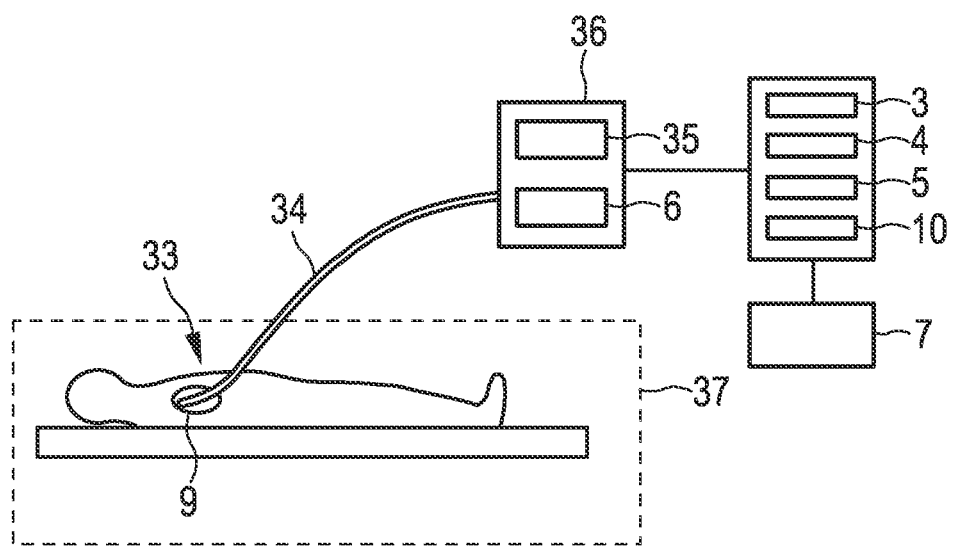
FIG. 6 shows schematically and exemplarily an other embodiment of an apparatus for being used for detecting a property of an object.

In an embodiment, the apparatus for being used for detecting a property of an object comprises preferentially a catheter for allowing the detection of a property of an object 9 located within a person 33 like the property of a heart as schematically and exemplarily shown in FIG. 6.

The apparatus comprises an ultrasound unit at a distal end of a catheter 34, i.e. at a catheter tip. The ultrasound unit (not shown in FIG. 6) is controlled by an ultrasound control unit 35, which forms together with the ultrasound unit an ultrasound signal providing unit. The ultrasound unit and the ultrasound control unit 35 are adapted to send out ultrasound pulses to the heart 9, to receive dynamic echo series after the ultrasound pulses have been reflected by the heart 9 and to generate the ultrasound signal depending on the received dynamic echo series.

At the distal end of the catheter 34 an energy application unit for ablating the object 9 is located. The energy application unit (not show in FIG. 6) comprises energy application elements like electrodes for applying electrical energy, in particular, radio-frequency energy, or like optical elements for applying light energy, for example, optical fibers and/or other optical elements.

The apparatus further comprises the control unit 6 for controlling the energy application element. The control unit 6 and the ultrasound control unit 35 are integrated in a main control unit 36. In other embodiments, the control unit 6 and the ultrasound control unit 35 can be separate control units. Furthermore, the control unit 6 can be further adapted to control a steering of the catheter tip, a sensing of the heart wall tissue and/or an irrigation. In this case, the catheter comprises a steering element, a sensing element and/or an irrigation element, respectively. These different control functions can be performed by any other number of control units, for example, by a single control unit or by two or more than two control units.

The apparatus further comprises the frequency determination unit 3, the filtering unit 4, the periodicity value determination unit 5, the lesion boundary determination unit 10 and the display 7.

Figure 7:
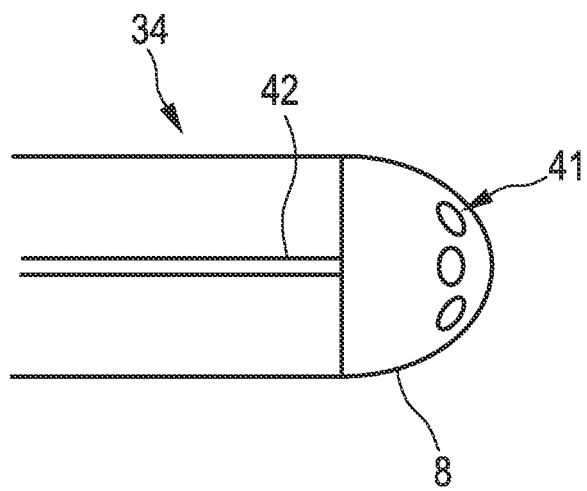
FIG. 7 shows schematically and exemplarily an embodiment of a catheter tip.

FIG. 7 shows schematically and exemplarily a tip of the catheter 34 in more detail. The catheter tip comprises an ablation electrode 8 for ablating cardiac tissue and ultrasound units 41, which are located within or at the ablation electrode 8. If the ultrasound units 41 are located within the ablation electrode 8, the ablation electrode 8 comprises openings for allowing the ultrasound units 41 to sense the cardiac tissue through the openings. In this embodiment, the ultrasound units 41 are arranged along a circular line around the tip of the ablation electrode 8. However, in other embodiments, the ultrasound units can also be arranged in another way. Furthermore, instead of several ultrasound units also a single ultrasound unit can be used for generating the ultrasound signal. The ultrasound units 41 and the ablation electrode 8 are connected with the main control unit 36 via a connection 42. The connection 42 comprises, for example, an electrical wire for providing electrical energy to the ablation electrode 8 and another wire for controlling the ultrasound units 41 and for transmitting the ultrasound signals from the ultrasound units 41 via the catheter 34 to the outside of the person 33. Although not shown in FIG. 7, the catheter can comprise further elements like an irrigation element, further sensing element like an electrical or optical sensing element, et cetera.

The apparatus shown in FIG. 6 is preferentially used in combination with a system for determining the position and/or orientation of the catheter, in particular, within the object 9, preferably, within a heart of a human being or an animal. In this embodiment, an imaging system like a magnetic resonance image system or an X-ray fluoroscopy system is used for determining the position and/or orientation of the catheter. This imaging system is indicated by the broken line 37 shown in FIG. 6. The catheter 34, in particular, the catheter tip can comprise elements for facilitating the determination of the orientation and/or position of the catheter by using the imaging system 37. For example, the catheter tip can comprise a tracking coil, if the catheter tip is used within a magnetic resonance imaging system, or elements that can be identified on an X-ray image and that are shaped such that a determination of the position and/or orientation of the catheter by using an X-ray fluoroscopy system is possible. The catheter tip can also comprise a location sensor for determining the position and/or orientation of the catheter, in particular, of the catheter tip within the object 9. By determining the position and/or orientation of the catheter within the object line, the lesion boundary can be determined and energy can be applied at known positions within the object 9.

Figure 8:
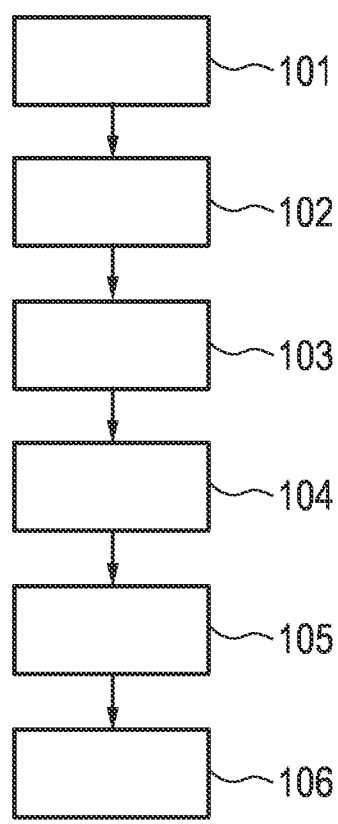
FIG. 8 shows a flowchart exemplarily illustrating an embodiment of a method for being used for detecting a property of an object.

In the following a method for being used for detecting a property of an object will exemplarily be described with reference to a flowchart shown in FIG. 8.

In step 101, an ultrasound signal is provided being indicative of a property of an object at one or several depths within the object and depending on time by an ultrasound unit. In step 102, the frequency of the periodic movement of the object, which is, in this embodiment, a heart of a person, is determined by the frequency determination unit 3. In step 103, the filtering unit temporarily filters the ultrasound signal for a constant depth with a band-pass which includes the determined frequency of the periodic movement. In step 104, the periodicity value determination unit determines a periodicity value being indicative of the temporal periodicity of the ultrasound signal for a constant depth. In particular, different ultrasound signal segments are determined from the ultrasound signal, which correspond each to a constant depth and to a temporal segmentation duration, and for each of the different ultrasound signal segments periodicity values are determined. Preferentially, for each of the ultrasound signal segments an auto-correlation function is calculated and the respective periodicity value is determined depending on the peak values of the non-zero shift peaks of the respective auto-correlation function. In an embodiment, the first peak value of a first peak at a non-zero shift location, which is neighbored to a peak at a zero shift location of the respective temporal auto-correlation, is determined as the respective periodicity value. In step 105, a lesion boundary is determined by the lesion boundary determination unit, which is generated by applying energy to the object, depending on the determined periodicity value. In particular, periodicity values, which have been determined for different times and different depths within the object, are compared with a predefined threshold, in order to determine at which depth and at which time a lesion boundary is present. In step 106, a two-dimensional representation of the periodicity values and preferentially also the determined lesion boundary can be shown on the display.

The periodicity value can be used for determining the lesion boundary, because the periodicity value describes the instability of the lesion front during the lesion formation process. The apparatus and method for being used for detecting a property of an object can be adapted to capture the lesion progress via a time-frequency analysis as described above. A periodicity value is determined which describes the dynamics of the transition that is caused by the heating process and break-up of compact healthy tissue structures during an ablation procedure. The time-frequency data are therefore expected to be different for a tissue region where the structure is not changing, i.e. where is either healthy or necrotic tissue, compared to a region that is undergoing a structure change due to heating. This difference in the time-frequency data can be reflected in the periodicity value. The periodicity value, in particular, the temporal auto-correlation, can capture the dynamic change of the spot where the structural break-up is taking place. The periodicity of the ultrasound signal caused by a periodic motion of the object, in particular, by cardiac motion, is disturbed, thereby showing a short period of more randomness in the ultrasound signal compared to the ultrasound signal of the same area right before the ablation. After the ablation, i.e. behind the lesion boundary, the periodic pattern may recover.

The apparatus and method for being used for detecting a property of an object can be used in several applications. For example, they can be used in tissue imaging during treatment of, for instance, cardiac arrhythmias and tumor ablation. However, they can also be used to determine properties of other objects not being the heart like other organs or other parts of a person or of an animal. Moreover, the apparatus and the method can also be adapted to be used for determining a property of a technical object. The apparatus and method for being used for detecting a property of an object can be adapted to be used to detect a structural change in applications like preparing meat, boiling eggs, drying of concrete et cetera.

Although in the above described embodiments the lesion boundary determination unit is adapted to determine the lesion boundary depending on one or several periodicity values only, the lesion boundary determination unit can also be adapted to determine the lesion boundary based on further features obtained from the ultrasound signal. For example, neighboring vertical lines in an M-mode image can be correlated for determining a correlation value, wherein this correlation value and the periodicity value can be used together for determining whether in a respective region a lesion boundary is present or not. This feature or other features obtained from the ultrasound signal can be used together with the one or several periodicity values for determining a lesion boundary. For example, a classifier like a decision tree classifier can be used to determine whether a region comprises a lesion boundary or not depending on the feature vector comprising one or several periodicity values and the other features. The classifier can be trained by calibration, wherein ultrasound signals of tissue having a lesion boundary at known positions are used for determining feature vectors and wherein the classifier is trained such that the classifier determines locations of the lesion boundary, which match as good as possible the known locations of the lesion boundary.

Although in the above described embodiments the apparatus comprises a frequency determination unit 3 for determining the frequency of the periodic movement of the object, in particular, of the heart, in other embodiments the frequency determination unit 3 does not need to be present. For example, the filtering unit 4 can temporarily filter the ultrasound signal for a constant depth with a predefined band-pass which includes expected possible frequencies of the periodic movement of the object. For example, if the object is a heart of a person, the band-pass can be 0.5 Hz to 3 Hz corresponding to 30 beats/min to 180 beats/min.

Although in the above described embodiments the periodicity value determination unit is adapted to determine the periodicity value depending on a temporal auto-correlation of the ultrasound signal for a constant depth, the periodicity value determination unit can also be adapted to determine a periodicity value, which is indicative of a degree of temporal periodicity of the ultrasound signal for a constant depth, in another way. For example, a frequency or spectrum analyses can be applied to the ultrasound signal, wherein a periodicity value can be determined based on the ultrasound signal within a predefined frequency range.

Although in the above described embodiments the ultrasound signal providing unit is a measurement unit which measures ultrasound signals, in other embodiments the ultrasound signal providing unit can also be a storing unit in which produced ultrasound signals are stored already or it can be an ultrasound signal receiving unit for receiving a generated ultrasound signal as an input which can be used by the further units for processing the ultrasound signal.

Although in the above described embodiments the apparatus for being used for detecting a property of an object comprises a filtering unit, the filtering unit is optional like the frequency determination unit. Also the lesion boundary determination unit is optional, wherein, if the apparatus for being used for detecting a property of an object does not comprise the lesion boundary determination unit, the periodicity values can, for example, be directly shown on the display or one or several periodicity values can be used as control parameter for controlling an application of energy.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations like the determination of a frequency of a periodic movement of the object, the filtering, the determination of a periodicity value and the determination of a lesion boundary performed by one or several units or devices can be performed by any other number of units or devices. For example, steps 102 to 105 can be performed by a single unit or by any other number of different units. The calculations and/or the control of the apparatus for being used for detecting a property of an object in accordance with the method for being used for detecting a property of an object can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an apparatus for being used for detecting a property of an object. An ultrasound signal providing unit provides an ultrasound signal, which is indicative of a property of the object at one or several depths within the object and which depends on time, and a periodicity value determination unit determines a periodicity value being indicative of a degree of temporal periodicity of the ultrasound signal for a constant depth. The temporal periodicity of the ultrasound signal at the respective constant depth, i.e. the periodicity value, depends on the property of the object at this depth and can therefore be used for detecting a property of the object.

The invention claimed is:

1. An apparatus for being used for detecting a property of an object, the apparatus (1) comprising:
    an ultrasound signal providing unit (2) for providing an ultrasound signal, which is indicative of a property of the object (9) at one or several depths within the object (9) and which depends on time,
    a periodicity value determination unit (5) for determining a periodicity value being indicative of a degree of temporal periodicity of the ultrasound signal for a constant depth, in order to detect the property of the object.

2. The apparatus as defined in claim 1, wherein the apparatus further comprises a lesion boundary determination unit (10) for determining a lesion boundary, which is generated by applying energy to the object (9), depending on the determined periodicity value.

3. The apparatus as defined in claim 2, wherein the lesion boundary determination unit (10) is adapted to determine the lesion boundary by thresholding the periodicity value.

4. The apparatus as defined in claim 2, wherein the apparatus (1) further comprises an energy application unit (8) for applying energy to the object (9) and a control unit (6) for controlling the energy application unit (8) depending on the determined lesion boundary.

5. The apparatus as defined in claim 1, wherein the ultrasound signal providing unit (2) is adapted to provide an M-mode image as the ultrasound signal.

6. The apparatus as defined in claim 1, wherein the object (9) is a periodically moving object and wherein the apparatus (1) further comprises a filtering unit (4) for temporally filtering the ultrasound signal, before determining the periodicity value, for a constant depth with a band-pass which includes a frequency of the periodic movement of the object (9).

7. The apparatus as defined in claim 6, wherein the apparatus (1) further comprises a frequency determination unit (3) for determining the frequency of the periodic movement of the object, wherein the filtering unit (4) is adapted to temporally filter the ultrasound signal for a constant depth with a band-pass which includes the determined frequency of the periodic movement.

8. The apparatus as defined in claim 1, wherein the periodicity value determination unit (5) is adapted to determine the periodicity value depending on a temporal auto-correlation of the ultrasound signal for a constant depth.

9. The apparatus as defined in claim 8, wherein the periodicity value determination unit (5) is adapted to determine the periodicity value depending on one or several peak values at non-zero shift locations of the temporal auto-correlation of the ultrasound signal for a constant depth.

10. The apparatus as defined in claim 9, wherein the periodicity value determination unit (5) is adapted to determine the periodicity value depending on a first peak value of a first peak at a non-zero shift location, which is neighbored to a peak at a zero shift location of the temporal auto-correlation of the ultrasound signal for a constant depth.

11. The apparatus as defined in claim 1, wherein the periodicity value determination unit (5) is adapted to determine different ultrasound signal segments, which correspond each to a constant depth and to a temporal segmentation duration, and to determine for the different ultrasound signal segments periodicity values.

12. The apparatus as defined in claim 11, wherein the apparatus (1) further comprises a lesion boundary determination unit (10) for determining a lesion boundary depending on the several periodicity values.

13. The apparatus as defined in claim 11, wherein the apparatus (1) further comprises a display (7) for showing the periodicity values depending on the depths and temporal positions of the respective ultrasound signal segments for which the periodicity values have been determined.

14. A method for being used for detecting a property of an object, the method comprising:
    providing an ultrasound signal, which is indicative of a property of the object at one or several depths within the object and which depends on time, by an ultrasound signal providing unit (2),
    determining a periodicity value being indicative of a degree of temporal periodicity of the ultrasound signal for a constant depth by a periodicity value determination unit (5), in order to detect the property of the object.

15. A non-volatile computer program product having encoded thereon a computer program comprising:
    program code means for causing an ultrasound signal providing unit (2) to provide an ultrasound signal, which is indicative of a property of the object (9) at one or several depths within the object (9) and which depends on time, and
    program code means for causing a periodicity value determination unit (5) to determine a periodicity value being indicative of a degree of temporal periodicity of the ultrasound signal for a constant depth, in order to detect the property of the object.

* * * * *